United States Patent [19]
DeLuca et al.

[11] Patent Number: 4,512,925

[45] Date of Patent: Apr. 23, 1985

[54] 1,23-DIHYDROXYVITAMIN D COMPOUNDS

[75] Inventors: Hector F. DeLuca; Heinrich K. Schnoes; Seok-Ho Lee, all of Madison, Wis.

[73] Assignee: Wisconsin Alumini Research Foundation, Madison, Wis.

[21] Appl. No.: 531,964

[22] Filed: Sep. 14, 1983

[51] Int. Cl.$^3$ .................................................. C07J 9/00
[52] U.S. Cl. ................................. 260/397.2; 260/397.1
[58] Field of Search ....................................... 260/397.2

[56] References Cited
U.S. PATENT DOCUMENTS 4,226,788 10/1980 DeLuca et al. ................... 260/397.2
4,260,549 4/1981 DeLuca et al. ................... 260/397.2

Primary Examiner—Elbert L. Roberts
Attorney, Agent, or Firm—Howard W. Bremer

[57] ABSTRACT

This invention provides novel 1,23-dihydroxyvitamin D compounds, a process for preparing such compounds of novel intermediates in such process.

As indicated by its binding affinity for the 1α,25-dihydroxyvitamin $D_3$ receptor protein, the compounds of this invention would function as effective substitutes for vitamin D and certain vitamin D metabolites for the regulation of calcium and phosphorous metabolism and for treatment of bone-related diseases.

28 Claims, No Drawings

1,23-DIHYDROXYVITAMIN D COMPOUNDS

DESCRIPTION

Technical Field

This invention relates to hydroxylated vitamin D analogs. More specifically, this invention relates to novel 1α,23-dihydroxyvitamin D compounds, and to methods and novel intermediates utilized for their preparation.

BACKGROUND

For the regulation of calcium and phosphate metabolism in the animal or human and for the regulation of normal bone growth, development and maintenance, the metabolites of vitamin D are essential agents. In the normal animal or human, these bone-related processes are regulated by 1α,25-dihydroxyvitamin $D_3$, a metabolite formed from vitamin $D_3$ by hydroxylation at carbon 25 and then at carbon 1. This discovery has stimulated much activity aimed at preparing the natural metabolite and structural analogs thereof. Results of these efforts are summarized in several reviews (e.g. Yakhimovich, Russian Chem. Rev. 49, 371 (1980); DeLuca et. al. Topics in Current Chemistry, Vol. 83, p. 1 (1979); Ann. Rev. Biochem. 52, 411 (1983)). Important examples of synthetic analogs of the natural hormone include 1α-hydroxyvitamin $D_3$ (U.S. Pat. No. 3,741,996), 1α-hydroxyvitamin $D_2$ (U.S. Pat. No. 3,907,843), 3-deoxy-1α,25-dihydroxyvitamin $D_3$ (U.S. Pat. No. 4,264,512), 10,19-dihydro-1α-hydroxyvitamin $D_3$ compounds (U.S. Pat. No. 4,159,326), 1α,24-dihydroxyvitamin $D_3$ (U.S. Pat. No. 4,022,891), 24,24-difluoro-1α,25-dihydroxyvitamin $D_3$ (U.S. Pat. Nos. 4,226,788, 4,284,577), 26,26,26,27,27,27-hexafluoro-1α,25-dihydroxyvitamin $D_3$ (U.s. Pat. No. 4,358,406) and other side-chain or ring A fluoro analogs (U.S. Pat. Nos. 4,069,321; 4,224,230; 4,307,025).

DISCLOSURE OF INVENTION

A class of analogs not known heretofore are 1α,23-dihydroxyvitamin D compounds. These compounds, characterized by hydroxy substitution at carbons 1 and 23 (instead of carbon 25) of the vitamin D skeleton, have now been prepared by chemical processes as set forth herein. Specifically, the novel compounds of this invention may be represented by the formulae shown below:

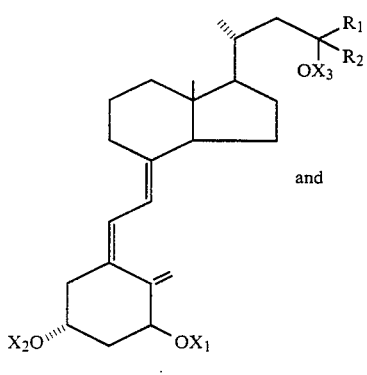

and

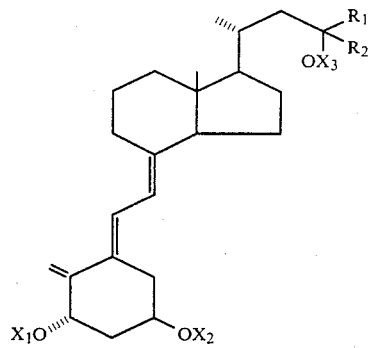

wherein $R_1$ and $R_2$ are selected from the group consisting of hydrogen and alkyl and where $X_1$, $X_2$ and $X_3$ are selected from hydrogen or a hydroxy-protecting group.

Important examples of such analogs are the compounds where $R_1$ is hydrogen and $R_2$ is isobutyl (i.e. 1α,23-dihydroxyvitamin $D_3$ and its 5,6-trans-isomer), or where $R_1$ is hydrogen and $R_2$ is methyl, ethyl, propyl, isopropyl or butyl, as well as the compounds where both $R_1$ and $R_2$ represent an alkyl group, e.g. where $R_1$ and $R_2$ are methyl, or where $R_1$ is methyl, and $R_2$ is ethyl, propyl, butyl or isobutyl.

In this specification and in the claims, the word "alkyl" denotes a lower hydrocarbon radical of from 1 to 5 carbons, in all isomeric forms, e.g. methyl, ethyl, propyl, butyl, isopropyl, isobutyl, sec-butyl, pentyl, etc. A hydroxy-protecting group is any of the common organic groupings used for protection of hydroxy functions, e.g. acyl, alkylsilyl, methoxy-methyl, tetrahydropyranyl. Of particular interest are acyl protecting groups, i.e. alkanoyl groups of from 1 to 5 carbons, such as formyl, acetyl, propionyl, etc. or aromatic acyl groups such as benzoyl, or halo, nitro, or alkyl substituted benzoyl groups, or carboxyalkanoyl groups of from 1 to 6 carbons, such as oxalyl, malonyl, succinyl, valeryl, adipyl or diglycolyl.

The analogs identified above are thus characterized by possessing the important 1α-hydroxy (or protected-hydroxy) group and by side chain structures having a 23-hydroxy (or protected hydroxy) function which may be primary, secondary or tertiary, i.e. the hydrocarbon substituents $R_1$ and $R_2$ at carbon 23 may be both hydrogen, or hydrogen and alkyl, or both alkyl, as illustrated below:

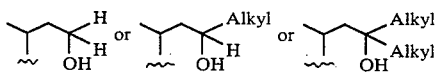

It is also to be noted that when in the above structures the two substituents at carbon 23 are both alkyl these alkyl groups may be identical or different, e.g. $R_1$ and $R_2$ may both represent methyl, ethyl, isopropyl, butyl, etc., or they may represent any combination of two different substituents such as methyl and ethyl, methyl and isopropyl, ethyl and propyl, etc.

In the compounds of this invention, the side chain hydroxy group, which occurs in the natural metabolite, 1α,25-dihydroxyvitamin $D_3$, at the 25-position, occurs at the 23-position. Despite this important structural change, it has been found that the 1,23-dihydroxy analogs of this invention exhibit pronounced bio-potency as expressed, in particular, by their high binding affinity to the cytosolic receptor protein in intestine, a property which is known to be important for high in vivo activity.

The 1,23-dihydroxy compounds can be prepared by a series of process steps which are more fully described below and in the process schematics.

The compounds can be prepared from a common starting material, such as the cyclovitamin D-23-aldehyde of structure 1a shown in Process Scheme I. In this formula, the radical Z represents a lower hydrocarbon radical (alkyl) as defined above. Generally and conveniently, Z represents methyl, but homologs where Z is, for example, ethyl, propyl, isopropyl, etc. are also suitable starting materials for the present process. This starting material may be converted to the desired final products illustrated above by three major process steps: (a) introduction of the desired C-23 substituents ($R_1$, $R_2$) by alkylation or reduction; (b) introduction of the C-1-hydroxy function, and (c) solvolysis to obtain the 5,6-cis and 5,6-trans 1α,23-dihydroxyvitamin D products. In principle, these three main process steps can be carried out in any desired order (e.g. C-23-substituent introduction, followed by 1α-hydroxylation, followed by solvolysis, or 1α-hydroxylation, followed by solvolysis, followed by 23-substituent introduction, etc.), and the choice of a specific sequence of steps is a matter of convenience dictated in part by the nature of the specific target compound to be prepared, as will be evident to those skilled in the art.

For example, 1α-hydroxylation of compound 1a with $SeO_2$ and a hydroperoxide (e.g. $H_2O_2$, or an alkyl hydroperoxide) according to the procedure of DeLuca et al., U.S. Pat. No. 4,195,027, gives the 1α-hydroxy intermediate 2a ($X_1$=H). This compound is then solvolyzed, preferably in a medium containing an organic carboxylic acid (e.g. acetic, formic, propionic acid, see DeLuca et al., U.S. Pat. No. 4,260,549) to obtain in admixture the 5,6-cis-vitamin D compound represented by structure 3a ($X_1$=H; $X_2$=acyl) and the 5,6-trans compound of structure 4a ($X_1$=H, $X_2$=acyl), where the acyl group ($X_2$) corresponds to the acyl moiety of the acid used in the solvolysis reaction. These cis and trans compounds can be separated at this stage (e.g. by chromatography using thin layer plates, or high performance columns) to give compounds 3a and 4a individually. These C-3-monoacylates can be used directly for the next step of the process, or, if desired, the 3-O-acyl groups in compounds 3a or 4a can be removed by base hydrolysis (e.g. 5%–10% KOH) to give 3a and 4a where $X_1$ and $X_2$=H, or the free 1-hydroxy group may be acylated under conventional conditions to provide 3a and 4a where $X_1$ and $X_2$ are acyl groups, which may be the same or different.

Treatment of compound 3a (where $X_1$ and $X_2$ may be acyl or H) with a reductant (e.g. $NaBH_4$ or $LiAlH_4$ or similar reducing agent) provides one of the desired analogs, compound 3b (where $R_1$ is hydrogen and $X_1$ and $X_2$ may be acyl or hydrogen, depending on the nature of 3a and the reductant used, and $X_3$ is hydrogen). Analogous reduction of the trans compound 4a gives analog 4b where $R_1$ represents hydrogen (see Process Scheme I). Any acyl groups present in 3b or 4b thus prepared may be removed by simple base hydrolysis to obtain the corresponding free hydroxy compounds.

A suitable alternative sequence to the above compounds is for example, reduction of 1a to provide intermediate 1b ($R_1$=H) followed by 1α-hydroxylation to 2b ($R_1$=H) and solvolysis and final acyl hydrolysis. Likewise, a sequence involving reduction of 2a to the corresponding C-23-primary alcohol (2b, $R_1$=H) followed by solvolysis can be used effectively.

The preparation of 23-monoalkyl analogs can be achieved by alkylation of the intermediate 3a ($X_1$=$X_2$=acyl or H) with an alkyl-Grignard reagent in an ether solvent at a temperature ranging from 0° C. to reflux, or the corresponding.) alkyl-lithium reagents (methyl lithium, ethyl lithium, etc.) to provide the analogs of general structure 3b where $R_1$ is an alkyl group introduced by the Grignard or alkyl-lithium reagent. For example:

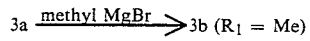

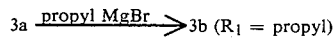

In all of the above examples, $X_1$ and $X_2$ in compound 3a may be hydrogen or acyl, whereas $X_1$, $X_2$ and $X_3$ in the product of type 3b are all hydrogen, since acyl groups (if present in the starting material) are removed during the Grignard reaction step.

Analogous alkylation of the 5,6-trans compound 4a gives the 5,6-trans-1,23-dihydroxy analogs of structure 4b where $R_1$ is an alkyl group.

As shown in Process Scheme I, the C-23-alkyl analogs of structure 3b or 4b (where $R_1$=alkyl) can also be conveniently prepared by an alternative route. Thus initial reaction of cyclovitamin D starting material 1a with the appropriate Grignard or alkyl lithium reagent, gives the 23-hydroxycyclovitamin intermediate of structure 1b (where $R_1$=alkyl and $X_3$=H). Suitable Grignard reagents are for example, methylmagnesium bromide, ethyl magnesium bromide, propyl- and isopropylmagnesium bromide, butyl- and isobutyl magnesium bromide, or sec. butyl magnesium bromide, and the use of such reagents then gives a series of 23-hydroxy compounds of general structure 1b, where $R_1$ is the alkyl group (i.e. methyl, ethyl, propyl, isopropyl, butyl, isobutyl, or sec. butyl, respectively) introduced by the Grignard reagent.

Subsequent 1α-hydroxylation of 1b, under the conditions cited above, then provides the corresponding 1α,23-dihydroxy cyclovitamin D compound of structure 2b (where $R_1$=alkyl and $X_1$ and $X_3$ are hydrogen). Solvolysis of compound 2b, using conditions analogous to those described above gives the 3-O-acyl derivatives of the compounds represented by structures 3b and 4b ($R_1$=alkyl, $X_1$ and $X_3$=H, $X_2$=acyl), as a mixture. Separation of this mixture provides analogs 3b and the 5,6-trans analog 4b in pure form (where $R_1$=alkyl, $X_1$ and $X_3$=H, $X_2$=acyl). Acyl hydrolysis then gives the corresponding free hydroxy compounds. If desired, the mixture of the 3-O-acyl derivatives of 3b and 4b as obtained by the solvolysis reaction may also be hydrolyzed directly to give a mixture of 3b and 4b (where $X_1$, $X_2$ and $X_3 = H$), which is then separated to provide the desired cis compound 3b ($R_1$=alkyl, $X_1$, $X_2$, $X_3 = H$) and the trans compound 4b ($R_1$=alkyl, $X_1$, $X_2$, $X_3 = H$).

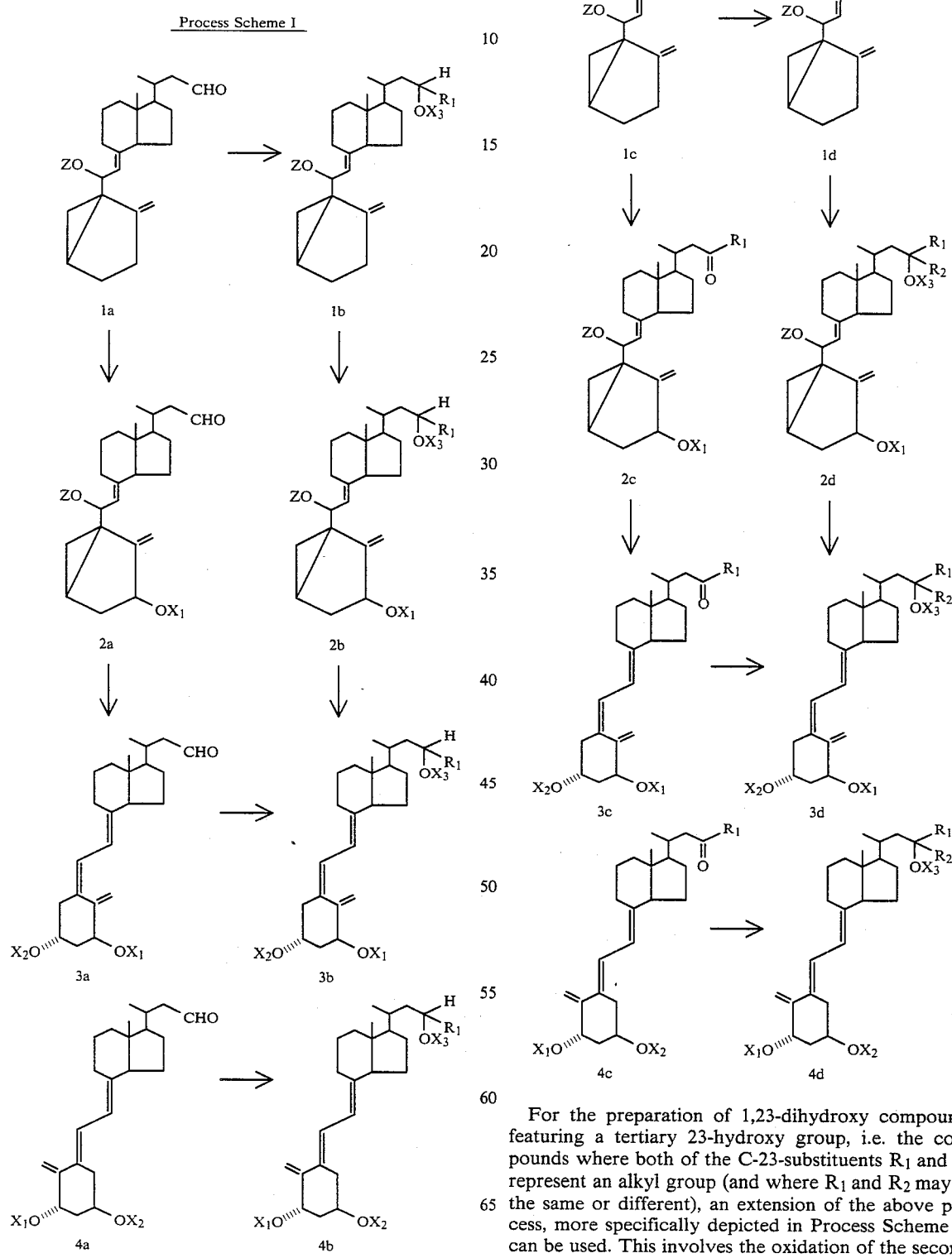

For the preparation of 1,23-dihydroxy compounds featuring a tertiary 23-hydroxy group, i.e. the compounds where both of the C-23-substituents $R_1$ and $R_2$ represent an alkyl group (and where $R_1$ and $R_2$ may be the same or different), an extension of the above process, more specifically depicted in Process Scheme II, can be used. This involves the oxidation of the secondary 23-hydroxy group in a cyclovitamin D intermediate of general structure 1b (where $R_1$=alkyl, and $X_3$=H) to obtain the corresponding 23-keto-intermediate, i.e. the compounds of general structure 1c, shown in Process Scheme II, where $R_1$ is the same alkyl group present in the precursor of formula 1b. This oxidation is accomplished with mild oxidants suitable for hydroxy to ketone conversions, for example, chromium oxide reagents (e.g. pyridinium dichromate, in dimethylformamide solution) or sulfur trioxide pyridine complex in dimethylsulfoxide and triethylamine, at about room temperature or below. Subjecting this keto intermediate of structure 1c to a reaction with a Grignard reagent (alkyl magnesium halide) or with an organo-metal reagent (alkyl-lithium) under conditions analogous to those used for the conversion of 1a to 1b, then provides a 23-tertiary hydroxy cyclovitamin intermediate, i.e. a compound of general structure 1d in which $X_3$ is hydrogen and where both $R_1$ and $R_2$ represent an alkyl group (which may be the same or different, depending on the nature of $R_1$ present in compound 1c and the nature of the alkyl group in the Grignard reagent or organo-metal reagent used for the conversion of 1c to 1d).

For example:

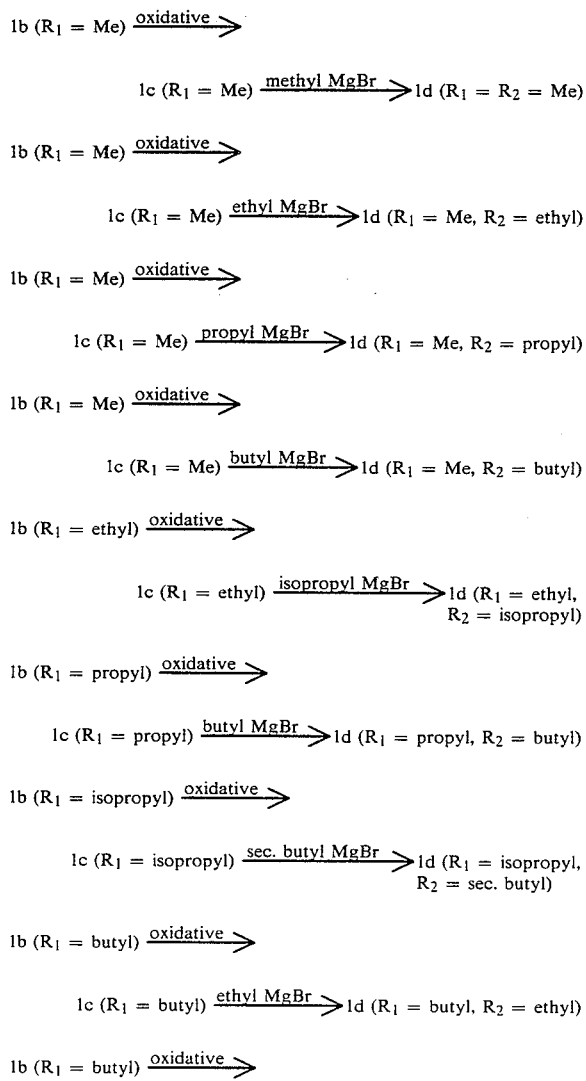

The 23-hydroxy function may be acylated to provide the corresponding acyloxy derivative (1d, where $X_3$=acyl) but such acylation is not required for the conversions which follow. Subsequent allylic hydroxylation of the tertiary-hydroxy compound of type 1d ($R_1$ and $R_2$=alkyl and $X_3$=hydrogen or acyl) at carbon 1, using the conditions (SeO$_2$/hydroperoxide) mentioned above then provides the corresponding 1α,23-dihydroxy cyclovitamin D compound (or the 23-acylates) of structure 2d ($R_1$ and $R_2$=alkyl). Further conversion of the latter intermediate along the lines described above for the case of the 23-secondary-hydroxy analog, namely, solvolysis to obtain a mixture of 5,6-cis and 5,6-trans-1,23-dihydroxyvitamin D compounds as the 3-O-acylates, separation of this mixture, to give the pure 3-O-acylates (compounds 3d and 4d, where $X_1$=hydrogen, $X_2$=acyl, and $X_3$=hydrogen or acyl) and hydrolysis of the acyl groups in each compound to obtain the 1α,23-dihydroxyvitamin D analog of structure 3d and the 5,6-trans-1α,23-dihydroxyvitamin D compound of structure 4d (where $R_1$ and $R_2$ represent alkyl, and where $X_1$, $X_2$, and $X_3$ are hydrogen).

As shown in Process Scheme II, the 23-keto intermediate (1c, $R_1$=alkyl) may also be directly 1α-hydroxylated to give compound 2c ($R_1$=alkyl, $X_1$=H), and solvolysis of that material, followed by separation of the cis and trans isomers (3c and 4c) and alkylation of each then provides an alternate route to the tertiary 23-hydroxy products (3d and 4d, where $R_1$ and $R_2$ are alkyl), whereas hydride reduction of 3c or 4c would provide the secondary 23-hydroxy compounds of structures 3b or 4b respectively (Process Scheme I) where $R_1$ is alkyl. These process steps are conducted in a fashion analogous to the equivalent process steps (i.e. the conversion of 1a→2a→3a/4a, etc.) already described above.

The reaction sequences described in the preceding and outlined in Process Schemes I and II thus provide the full array of the 23-primary, secondary or tertiary 1α,23-dihydroxyvitamin D compounds indicated by the general structures shown above. It should be noted that certain of the analogs discussed above, for example, 23-primary or 23-tertiary 1α,23-dihydroxyvitamin D analogs can also be prepared conveniently from an alternative starting material, namely the 1α-hydroxyvitamin D-23-esters (1α,3β-dihydroxy-24-nor-9,10-seco-5,7,10(19)-cholatrien-23-oic acid alkyl esters), represented by the structure shown below:

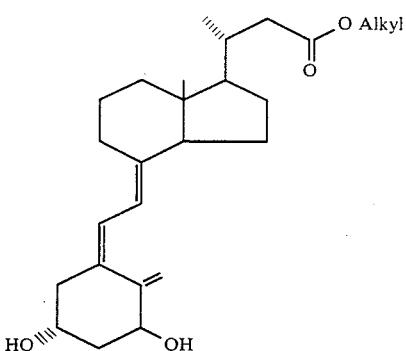

Such esters are known compounds (DeLuca et al. U.S. Pat. No. 4,209,634). Reduction of the 23-ester function in the compound shown above with, for example, lithium aluminum hydride, produces directly the corresponding 23-primary alcohol, i.e. the 1α,23-dihydroxyvitamin D analog of structure 3b (Process Scheme I) where $R_1$, $X_1$, $X_2$ and $X_3$ are hydrogen.

Alternatively, treatment of the ester shown above with an alkyl Grignard reagent leads to the 23-tertiary alcohol, i.e. the 1α,23-dihydroxyvitamin D compound of structure 3d (Process Scheme II) where $R_1$ and $R_2$ are both alkyl, and whereby, in this case, the two alkyl groups introduced are necessarily identical.

The 5,6-cis-vitamin-1α,23-dihydroxyvitamin D analogs thus prepared from the 23-ester shown above can be transformed into the corresponding 5,6-trans-isomers (general structure 4b or 4d) by the iodine-catalyzed double bond isomerization procedure of Verloop et al. [Rec. Trav. Chim. Pays-Bas 78, 1004 (1969)].

If the hydroxy-protected derivatives of products 3b, 4b, 3d or 4d are desired for therapeutic or other applications, they can be prepared from the free hydroxy compounds by conventional derivatization reactions known in the art. For example, a compound of structure 3b or 3d, where $X_1$, $X_2$ and $X_3$ represent hydrogen is readily acetylated to give the corresponding 1,3,23-tri-acetate, by treatment with acetic anhydride in pyridine and other acylates of 3b and 3d or 4b and 4d are similarly prepared by treatment with the appropriate acyl anhydride or acyl chloride at room temperature or elevated temperature according to known procedures.

In addition, it should be noted that the 3-O-acyl derivatives of the compounds of general structures 3 and 4 ($X_1$ and $X_3$=H, $X_2$=acyl) are of course obtained as immediate products of the solvolysis reaction, and other partially or completely acylated derivatives of the final products can be obtained if desired by the use of acylated intermediates in the reaction process. For example, intermediate 1b or 1d (where $R_1$ and $R_2$ represent alkyl, and $X_3$=H) can be acylated by standard procedures to the 23-acyl derivative (compound 1b or 1d, where $X_3$=acyl) and from these intermediates after hydroxylation to 2b or 2d, respectively ($X_1$=H, $X_3$=acyl) and solvolysis, the 3,23-diacyl compounds 3b or 3d (where $X_2$ and $X_3$ are acyl groups which may be the same or different, and $X_1$=H) and 4b or 4d ($X_2$ and $X_3$=acyl, $X_1$=H) are obtained. Similarly, acylation of the 23-acylates of 2b or 2d ($X_1$=H, $X_3$=acyl) to the corresponding 1,23-diacyl intermediate (compounds 2b or 2d, where $X_1$ and $X_3$=acyl) would provide, after solvolysis, the 1,3,23-tri-O-acylated products of structures 3b, 4b or 3d, 4d. Alternatively, selective acylation of the dihydroxy compounds 2b or 2d ($X_1$ and $X_3$=H) to the 1-O-acyl intermediate (2b or 2d, where $X_1$=acyl, $X_3$=H) followed by solvolysis yields 1,3-di-O-acyl derivatives ($X_1$ and $X_2$=acyl, $X_3$=H) of the final products (3b, 4b, 3d, 4d) and analogous 1,3-diacylates can be obtained by the 1,3-di-acylation of compounds of type 3a and 3c (or 4a and 4c) followed by borohydride reduction of the aldehyde or keto group.

It is to be noted also that whenever the substituents $R_1$ and $R_2$ at carbon 23 in the above-described compounds are not identical, said compounds will generally occur as a mixture of diastereomers (the 23R and 23S-epimers) and thus final products 3b and 4b (or 3d and 4d) will be obtained in mixtures of epimers, characterized by the R or S stereochemistry at carbon 23. If desired, these epimers may be separated (preferably by high performance liquid chromatography at the stage of the final product) to obtain the 23R and the 23S epimers in pure form. For example, reaction of aldehyde 1a with isobutylmagnesium bromide gives the cyclovitamin D intermediate 1b ($R_1$=isobutyl) as a mixture of the 23R and 23S-epimers. Further conversion of that mixture, by 1α-hydroxylation, solvolysis and acyl hydrolysis as discussed above, then provides four compounds, the 23R and S epimers of 3b ($R_1$=isobutyl) and the 23R and S epimers of 4b ($R_1$=isobutyl). These compounds can be separated, advantageously by high pressure liquid chromatography, to obtain each of the epimers in pure form. However, in many pharmaceutical applications, these C-23-epimers of 3b and 4b (or 3d and 4d) may also be used as the epimeric mixtures and separation is essential only when the pure 23-R and S-isomers are desired.

The starting material, the cyclovitamin D-23-aldehyde of structure 1a utilized in Process Scheme I is itself a novel compound. Its preparation is described below by an illustrative working example.

The 1α,23-dihydroxyvitamin D analogs of this invention exhibit high binding affinity for the 1α,25-dihydroxyvitamin $D_3$ receptor protein occurring in intestine and other vitamin D responsive tissues. Present evidence indicates that effective binding of a vitamin D metabolite or analog to this protein is a key step for expression of in vivo activity. Consequently, the remarkable binding potency of the compounds of this invention indicate that they can be used effectively as substitutes for the known vitamin D metabolites for the regulation of calcium and phosphorus metabolism in mammals and for the prevention or cure of bone-related diseases.

The present invention is more specifically described by the following examples which are intended to be illustrative only. In the examples, chemical products identified by numbers (e.g. compound 1a, 2a, 3b, 4d, etc.) refer to the structures similarly numbered in Process Schemes I or II. All the products and intermediates shown in Process Schemes I and II, are novel compounds.

EXAMPLE 1

Preparation of starting material, cyclovitamin D-23-aldehyde of structure 1a (Z=Me)

An ethanolic ethereal solution of diazomethane ($CH_2N_2$), generated from N-methyl-N-nitroso-p-toluenesulfonamide ($CH_3C_6H_4SO_2N(CH_3)NO$; Diazald), was added dropwise to a suspension of (20S)-3β-acetoxy-5-pregnene-20-carboxylic acid (10.0 g, 25.7 mmole; m.p. 228°–231° C.) in 1:9 ethanol-ether at room temperature until all the solids dissolved and pale yellow color due to an excess diazomethane persisted. Excess diazomethane was removed with a stream of N₂ until the solution became colorless. Removal of solvent provided the desired methyl ester, (20S)-3β-acetoxy-5-pregnene-20-carboxylic acid methyl ester (10.3 g; Rf 0.63 on silica gel in 3:7 ethyl acetate-hexane; m.p. 140°–142° C.) in 99.4% yield. Mass spectrum, m/e (relative intensity) 402 (M⁺, 0), 342 (100), 327 (10), 283 (4), 255 (6), 239 (5), 234 (11), 221 (12), 213 (5); NMR (CDCl₃) δ0.70 (s, 18—H₃), 1.02 (s, 19—H₃), 1.19 (d, J=6.8 Hz, 21—H₃), 2.03 (s, 3—OCOCH₃), 4.60 (m, 3—H), 5.37 (br d, J=4.8 Hz, 6—H).

Conversion of this product to the corresponding 5,7-diene ester was accomplished by treating a stirred solution of the above compound (10.0 g, 24.8 mmole) in dry hexane (150 ml) containing finely divided sodium bicarbonate (10.0 g) and preheating to 80° C. under nitrogen with 1,3-dibromo-5,5-dimethylhydantoin (Dibromantin; 3.62 g, 12.4 mmole). After 20 minutes, the reaction was worked up in the usual manner. s-Collidine (2,4,6-trimethylpyridine; 6 g, 49.6 mmole) was added slowly to a stirred solution of the 7-bromo intermediate in dry xylene (100 ml). After heating at reflux under nitrogen for 90 minutes, the resulting mixture, containing 5,7-diene and 4,6-diene was dissolved in dry dioxane (120 ml) and heated at 70° C. under nitrogen. After addition of p-toluenesulfonic acid (1 g) in dry dioxane (30 ml), heating was continued for 30 minutes. Workup by fractional crystallization from ethyl acetate-hexane provided the 5,7-diene product (6.77 g; Rf 0.59 on silica gel in 1:1 ethyl acetate-hexane) in 68.0% yield: UV (C₂H₅OH) λ$_{max}$ 293 nm, 282, 272, 263; mass spectrum, m/e (relative intensity) 400 (M⁺, 2), 340 (100), 325 (19), 281 (7), 253 (15), 237 (14), 211 (8), 158 (61); NMR (CDCl₃) δ0.64 (s, 18—H₃), 0.96 (s, 19—H₃), 1.23 (d, J=6.6 Hz, 21—H₃), 2.04 (s, 3—OCOCH₃), 3.67 (s, 22—COOCH₃), 4.71 (m, 3—H), 5.40 (m(sharp), 7—H), 5.58 (m(sharp), 6—H).

Hydrolysis of the 3β-acetoxy function was accomplished by treating a stirred solution of the above product (2.4 g, 6.0 mmole) in 3:7 methanol-ether (70 ml) with finely powdered anhydrous potassium carbonate (2.5 g, 18.0 mmole) at room temperature under nitrogen for 5 hr. The mixture, diluted with ether (100 ml), was washed with water (3×30 ml), the washings were back-extracted with ether (1×50 ml), and the combined extracts were washed with saturated aqueous sodium chloride (2×30 ml), dried over anhydrous magnesium sulfate, filtered, and concentrated in vacuo to give 2.14 g (99.6% yield) of the hydroxy-ester, having the structure:

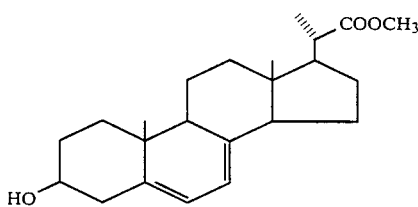

UV (EtOH) λ$_{max}$ 293 nm, 282, 272, 263; mass spectrum, m/e (relative intensity) 358 (M⁺, 100), 343 (5), 340 (8), 325 (81), 299 (54), 253 (12), 237 (19), 211 (18), 143 (51); NMR (CDCl₃) δ0.64 (s, 18—H₃), 0.95 (s, 19—H₃), 1.21 (d, J=6.8 Hz, 21—H₃), 3.66 (s, 22—COOCH₃), 5.39 (m(sharp), 7—H), 5.57 (m(sharp), 6—H).

A solution of the above 5,7-diene ester (1.5 g; 2×0.75 g, 4.18 mmole) in 1:4 dry benzene-ether (150 ml) was irradiated under nitrogen in a jacket around a double-walled, water-cooled quartz immersion well equipped with a nitrogen bubbler, a magnetic stirrer, and a Vycor filter using a Hanovia 608A36 quartz medium-pressure mercury vapor ultraviolet lamp. The reaction was monitored by high performance liquid chromatography (HPLC; Zorbax Sil analytical column) using 1% isopropanol-hexane at 265 nm. The quasi-photostationary state mixture contained lumisterol (8%), previtamin (63%), and provitamin (29%) which were eluted at 31 ml, 43 ml, and 53 ml, respectively. This mixture in ethanol, freshly distilled under nitrogen and saturated with nitrogen just prior to use, was heated to 70° C. for 3 hours under nitrogen, then cooled, and concentrated in vacuo. Purification by chromatography on Florisil (magnesium silicate; MgO 15.5%, SiO₂ 84%, Na₂SO₄ 0.5%) using ethyl acetate-hexane (stepwise elution; 5 to 25%) afforded the vitamin ester (0.774 g, 51.6% yield) of the structure shown below:

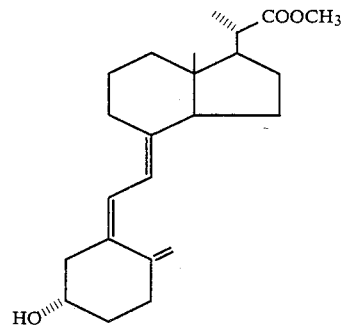

This compound was characterized by the following physical data: UV (C₂H₅OH) λ$_{max}$ 265 nm; mass spectrum, m/e (relative intensity) 358 (M⁺, 75), 340 (8), 325 (26), 299 (13), 253 (14), 237 (10), 211 (10), 136 (100), 118 (98); NMR (CDCl₃) δ0.56 (s, 18—H₃), 1.20 (d, J=6.8 Hz, 21—H₃), 3.65 (s, 22—COOCH₃), 3.94 (m, 3—H), 4.80 (d, J=1.2 Hz, 19Z—H), 5.04 (d, J=1.2 Hz, 19E—H), 6.03 (d, J=11.2 Hz, 7—H), 6.23 (d, J=11.2 Hz, 6—H).

A solution of the above vitamin ester (500 mg, 1.4 mmole) in dry pyridine (5 ml) was treated with freshly recrystallized p-toluenesulfonyl chloride (530 mg, 2.8 mmole) at 5° C. under nitrogen for 24 hours. The mixture was poured over ice, then extracted with ether (3×20 ml). The combined extracts were washed successively with 3% aqueous hydrochloric acid (2×10 ml), water (1×10 ml), saturated aqueous sodium bicarbonate (1×10 ml), saturated aqueous sodium chloride (2×10 ml), then dried over anhydrous magnesium sulfate, filtered, and concentrated in vacuo to yield the corresponding 3-p-toluenesulfonyl derivative (690 mg; Rf 0.56 on silica gel in 1:1 ethyl acetate-hexane) in 96.4% yield. Mass spectrum, m/e (relative intensity) 512 (M⁺, 7), 358 (16), 340 (88), 325 (23), 299(5), 281 (6), 253 (30), 158 (63), 118 (88), 91 (100); NMR (CDCl₃) δ0.54 (s, 18—H₃), 1.20 (d, J=6.8 Hz, 21—H₃), 2.46 (s, 3—O-SO₂C₆H₄CH₃), 3.66 (s, 22—COOCH₃), 4.70 (m, 3—H), 4.81 (br s, 19Z—H), 5.04 (br s, 19E—H), 5.97 (d, J=11.6 Hz, 7—H), 6.10 (d, J=11.6 Hz, 6—H), 7.34

(d, J=8.4 Hz, 3—OSO₂C₆H₄CH₃), 7.81 (d, J=8.4 Hz, 3—OSO₂C₆H₄CH₃).

The above toluenesulfonyl intermediate was then solvolyzed by addition (600 mg, 1.17 mmole) to a stirred suspension of finely divided sodium bicarbonate (600 mg) in anhydrous methanol (20 ml). The mixture was heated to 55° C. under nitrogen for 15 hours. The usual workup, followed by chromatography on silica gel using 30% ethyl acetate-hexane (double elution), provided 300 mg; 68.8% yield of the cyclovitamin D ester having the structure below:

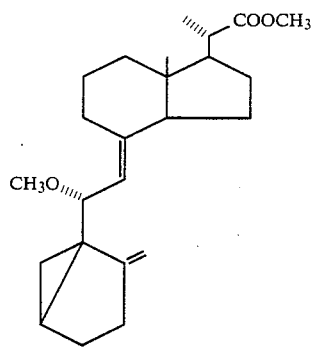

The product can be further purified by HPLC (Zorbax Sil semipreparative column) using 0.2% isopropanol-hexane. The product was characterized by the following data: mass spectrum, m/e (relative intensity) 372 (M⁺, 17), 340 (100), 253 (48), 221 (40), 135 (41), 119 (72); NMR (CDCl₃) δ0.54 (s, 18—H₃), 0.74 (m, 3—H), 0.91 (m, 4—H), 1.20 (d, J=7.2 Hz, 21—H₃), 3.25 (s, 6R—OCH₃), 3.65 (s, 22—COOCH₃), 4.15 (d, J=8.8 Hz, 6—H), 4.88 (br s 19Z—H), 5.00 (d, J=8.8 Hz, 7—H), 5.02 (br s, 19E—H).

A stirred solution of the above product (250 mg, 0.67 mmole; Rf 0.72 on silica gel in 5:95 methanol-chloroform) in ether was treated with lithium aluminum hydride, saturated in ether, at room temperature under nitrogen for 15 minutes. The usual workup gave the corresponding 22-alcohol (200 mg; Rf 0.58 on silica gel in 5:95 methanol-chloroform) in 86.5% yield. Mass spectrum, m/e (relative intensity) 344 (M⁺, 13), 312 (40), 253 (19), 193 (33), 135 (60), 119 (81); NMR (CDCl₃) δ0.56 (s, 18—H₃), 0.74 (m, 3—H), 0.92 (m, 4—H), 1.06 (d, J=6.3 Hz, 21—H₃), 3.26 (s, 6R—OCH₃), 3.66 (dd, J=2.8 Hz and 10.4 Hz, 22—H₂), 4.17 (d, J=9.2 Hz, 6—H), 4.89 (br s, 19Z—H), 5.01 (d, J=9.2 Hz, 7—H), 5.04 (br s, 19E—H).

A stirred solution of the above alcohol (160 mg, 0.46 mmole; Rf 0.26 on silica gel in 3:7 ethyl acetate-hexane) in dry pyridine (5 ml), cooled on an ice bath, was treated with freshly recrystallized p-toluenesulfonyl chloride (180 mg, 0.92 mmole) under nitrogen for 3 hours. Several chips of ice were added, and the mixture was stirred for 5 minutes to decompose the excess p-toluenesulfonyl chloride. The mixture was then poured into ice-cold water (5 ml), and extracted with ether (3×20 ml). The combined extracts were washed sequentially, with water (3×10 ml), saturated aqueous sodium bicarbonate (1×10 ml) and saturated aqueous sodium chloride (2×10 ml), then dried over anhydrous magnesium sulfate, filtered, and concentrated in vacuo to yield the 22-p-toluenesulfonate derivative (210 mg, Rf 0.46 on silica gel in 3:7 ethyl acetate-hexane) in 90.6% yield: mass spectrum, m/e (relative intensity) 498 (M⁺, 19), 483 (11), 466 (27), 294 (8), 135 (36), 119 (55), 91 (100).

A stirred solution of the above p-toluenesulfonyl intermediate (180 mg, 0.36 mmole) in dry dimethyl sulfoxide (10 ml) was treated with sodium cyanide (36 mg, 0.72 mmole) at 80° C. under nitrogen for 2 hours. The mixture was allowed to cool to room temperature, stirred for 1 hour, then poured over ice-saturated aqueous ammonium chloride (10 ml), and extracted with hexane (3×30 ml). The combined extract was washed with water (3×20 ml), saturated aqueous sodium chloride (2×20 ml), then dried over anhydrous magnesium sulfate, filtered (it can also be decolorized with activated charcoal, then filtered through Celite as a filter-aid), and concentrated in vacuo. Purification by chromatography on silica gel using 20% ethyl acetate-hexane (double elution) provided the desired cyclovitamin D-22-nitrile (100 mg; Rf 0.49 on silica gel in 3:7 ethyl acetate-hexane) in 78.3% yield. This product has the structure shown below.

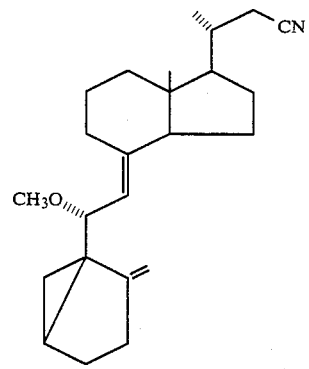

Mass spectrum, m/e (relative intensity) 353 (M⁺, 25), 338 (4), 321 (100), 306 (31), 135 (16), 119 (56); NMR (CDCl₃) δ0.57 (s, 18—H₃), 0.75 (m, 3—H), 0.92 (m, 4—H), 1.18 (d, J=6.8 Hz, 21—H₃), 3.26 (s, 6R—OCH₃), 4.15 (d, J=9.3 Hz, 6—H), 4.88 (br s, 19Z—H), 5.02 (d, J=9.3 Hz, 7—H), 5.04 (br s, 19E—H).

A stirred solution of the above nitrile (90 mg, 0.25 mmole) in dry benzene (10 ml) was cooled on an ice bath under nitrogen before diisobutylaluminum hydride ([(CH₃)₂CHCH₂]₂AlH; 0.25 ml, 1.5 mole solution in toluene) was added slowly. The ice bath was removed after the addition was complete and the reaction was allowed to proceed at room temperature for 30 minutes. Sufficient amount of methanol was then added carefully to decompose the aluminum salt complex, the mixture was poured over ice water, phases were separated, and the aqueous phase was extracted with ether (3×10 ml). The combined organic phase was washed with saturated aqueous sodium chloride (2×10 ml), dried over anhydrous magnesium sulfate, filtered, and concentrated in vacuo. Chromatography on silica gel using 25% ethyl acetate-hexane (double elution) afforded the desired cyclovitamin D-23-aldehyde having structure 1a (Z=Me) (Process Scheme I) (81 mg; Rf 0.52 on silica gel in 3:7 ethyl acetate-hexane) in 89.2% yield: mass spectrum, m/e (relative intensity) 356 (M⁺, 9), 324 (27), 135 (20), 119 (61); NMR (CDCl₃) δ0.59 (s, 18—H₃), 0.75 (m, 3—H), 0.92 (m, 4—H), 1.03 (d, J=6.4 Hz, 21—H₃), 3.27 (s, 6R—OCH₃), 4.17 (d, J=9.3 Hz, 6—H), 4.89 (br s, 19Z—H), 5.01 (d, J=9.3 Hz, 7—H), 5.04 (br s, 19E—H), 9.76 (m, 23—CHO).

EXAMPLE 2

Hydroxylation of 1a to 2a

Freshly distilled tert-butyl hydroperoxide (($CH_3)_3COOH$; 13 mg, 0.14 mmole) was added to a stirred suspension of selenium dioxide ($SeO_2$; 3.9 mg, 0.035 mmole) in dry methylene chloride (10 ml) under nitrogen. The mixture was stirred at room temperature until homogeneous (30 min), cooled on an ice bath, and cyclovitamin D aldehyde 1a (Z=Me) (25 mg, 0.07 mmole) in dry methylene chloride (1 ml) was added. The ice bath was then removed, and the reaction was allowed to proceed at room temperature for 1 hour. The reaction mixture was quenched by addition of 10% NaOH, diluted with ether and the phases (organic and aqueous) separated. The residue obtained by evaporation of the organic phase was subsequently chromatographed on silica gel using 40% ethyl acetate-hexane to give the 1α-hydroxy cyclovitamin D aldehyde of structure 2a, where Z=Me, $X_1$=H, (10 mg) in 38.2% yield: mass spectrum, m/e (relative intensity) 372 ($M^+$, 21), 340 (42), 299 (24), 135 (100).

EXAMPLE 3

Solvolysis of 2a to 3a and 4a

A stirred solution of product 2a as obtained in Example 2 (8 mg, 0.02 mmole) in glacial acetic acid (0.5 ml) was heated to 55° C. under nitrogen for 15 minutes. The resulting reaction product was poured over ice, neutralized with sodium bicarbonate and extracted with ether. Evaporation of the ether extract gave the mixture of the 3β-acetates (comprising compounds 3a and 4a, where $X_1$=H and $X_2$=acetyl) which was redissolved in ether (1 ml) and treated with 10% potassium hydroxide in methanol at room temperature under nitrogen for 15 minutes. The resulting product mixture was purified by high performance liquid chromatography (HPLC; Zorbax Sil semipreparative column, 6.2 mm×25 cm) using 5% isopropanol-hexane, to give compound 3a ($X_1$ and $X_2$=H): UV ($C_2H_5OH$) $\lambda_{max}$ 265 nm; mass spectrum, m/e (relative intensity) 358 ($M^+$, 28), 340 (15), 152 (49), 134 (100); NMR ($CDCl_3$) δ0.61 (s, 18—$H_3$), 1.04 (d, J=6.6 Hz, 21—$H_3$), 4.24 (m, 3—H), 4.44 (m, 1—H), 5.01 (d, J=1.2 Hz, 19Z—H), 5.34 (d, J=1.2 Hz, 19E—H), 6.03 (d, J=11.2 Hz, 7—H), 6.38 (d, J=11.2 Hz, 6—H), 9.76 (m, 23—CHO); and compound 4a ($X_1$ and $X_2$=H): UV ($C_2H_5OH$) $\lambda_{max}$ 273 nm; mass spectrum, m/e (relative intensity) 358 ($M^+$, 13), 340 (5), 152 (24), 134 (100); NMR ($CDCl_3$) δ0.62 (s, 18—$H_3$), 1.04 (d, J=6.4 Hz, 21—$H_3$), 4.25 (m, 3—H), 4.50 (m, 1—H), 4.98 (br s, 19Z—H), 5.13 (br s, 19E—H), 5.89 (d, J=10.8 Hz, 7—H), 6.58 (d, J=10.8 Hz, 6—H), 9.76 (m, 23—CHO).

EXAMPLE 4

Alkylation of 1a to give 1b

Isobutylmagnesium bromide (($CH_3)_2CHCH_2MgBr$) was prepared as follows: The apparatus was dried in an oven just prior to use. A 100 ml three-necked round bottom flask was fitted with a coil-type condenser, a dropping funnel with a pressure-equalizing side tube, and a magnetic stirrer. A trap was provided to the top of the condenser through a three-way tube. High purity dry nitrogen was introduced at the top of the condenser to be allowed to sweep through the apparatus and to escape at the mouth of the dropping funnel. A slight positive pressure of nitrogen was maintained when the funnel was closed as indicated by bubbles in the trap. Magnesium turnings (1.2 g, 0.05 mole) were placed in the flask, nitrogen was passed through for 30 minutes to displace air and to ensure elimination of any moisture, and isobutyl bromide (($CH_3)_2CHCH_2Br$; 6.8 g, 0.05 mole) in ether was introduced dropwise through the funnel with stirring after the nitrogen flow was reduced to a barely perceptible rate. The reaction was allowed to proceed for 4 hours. The final volume was adjusted to 50 ml.

Isobutylmagnesium bromide (0.5 ml, 0.5 mmole; 1.0 mole solution in ether) was added slowly to a stirred solution of 1a (35 mg, 0.1 mmole) (see Example 1) in ether (10 ml) under nitrogen. The mixture was refluxed at room temperature for 24 hours, then saturated aqueous ammonium chloride was added slowly from a dropping funnel at a rate controlled by the rapidity of refluxing to reach a point where a clear separation occurs. The mixture was allowed to settle for several minutes, the supernatant was decanted, and the precipitate was washed with several portions of fresh ether. The combined ethereal solutions were dried over anhydrous magnesium sulfate, filtered, and concentrated in vacuo. Chromatography on silica gel using 20% ethyl acetate-hexane (double elution) gave product 1b ($R_1$=isobutyl, $X_3$=H, Z=Me) (27 mg; Rf 0.50 on silica gel in 3:7 ethyl acetate-hexane) in 66.3% yield: mass spectrum, m/e (relative intensity) 414 ($M^+$, 16), 382 (83), 253 (50), 135 (45), 119 (95).

Treatment of compound 1a (Z=methyl) with ethylmagnesium bromide, under conditions analogous to those described above, gives product 1b ($R_1$=ethyl, $X_3$=H, Z=methyl).

Treatment of compound 1a (Z=methyl) with isopropylmagnesium bromide, under the above described conditions, gives product 1b ($R_1$=isopropyl, $X_3$=H, Z=methyl).

EXAMPLE 5

Hydroxylation of 1b to 2b

Freshly distilled tert-butyl hydroperoxide (($CH_3)_3COOH$; 11 mg, 0.12 mmole) was added to a stirred suspension of selenium dioxide ($SeO_2$; 3.3 mg, 0.03 mmole) in dry methylene chloride (10 ml) under nitrogen. The mixture was stirred at room temperature until homogeneous (30 minutes), cooled on an ice bath, and product 1b ($R_1$=isobutyl) from Example 4 (25 mg, 0.06 mmole) dissolved in dry methylene chloride (1 ml), was added. The ice bath was then removed, the reaction was allowed to proceed at room temperature for 1 hour, and 10% aqueous sodium hydroxide (5 ml) was added to quench the reaction. The mixture was diluted with ether (30 ml), phases were separated, and the organic phase was washed successively with 10% aqueous sodium hydroxide (3×5 ml), water (2×5 ml), saturated aqueous sodium chloride (2×5 ml), then dried over anhydrous magnesium sulfate, filtered, and concentrated in vacuo. Purification by chromatography on silica gel using 40% ethyl acetate-hexane yielded 12.2 mg (41%) of product 2b ($R_1$=isobutyl, $X_1$ and $X_3$=H, Z=Me): mass spectrum, m/e (relative intensity) 430 ($M^+$, 22), 412 (5), 398 (44), 380 (15), 357 (17), 135 (100); NMR ($CDCl_3$) δ0.57 (s, 18—$H_3$), 0.64 (t, J=4.6 Hz, 3—H), 0.92 (d, J=6.5 Hz, 26—$H_3$ and 27—$H_3$), 0.98 (d, J=6.4 Hz, 21—$H_3$), 3.26 (s, 6R—$OCH_3$), 3.79 (m, 23—H), 4.20 (m, 6—H), 4.23 (m, 1—H), 4.98 (m, 7—H), 5.17 (d, J=1.2 Hz, 19Z—H), 5.24 (d, J=1.2 Hz, 19E—H).

EXAMPLE 6

Solvolysis of 2b to 3b and 4b

A stirred solution of the product of Example 5 (10 mg, 0.023 mmole) in glacial acetic acid (0.5 ml) was heated to 55° C. at reflux under nitrogen for 15 minutes. The mixture was poured over ice, then ice-cold saturated aqueous sodium bicarbonate was added cautiously to neutralize, and the mixture was extracted with ether (3×10 ml). The combined extract was washed with water (1×5 ml), saturated aqueous sodium chloride (2×5 ml), then dried over anhydrous magnesium sulfate, filtered, and concentrated in vacuo.

The mixture of the 3$\beta$-acetates (compounds 3b and 4b, where $R_1$=isobutyl, $X_1$ and $X_3$=H, $X_2$=acetyl) in ether (1 ml) was treated with 10% potassium hydroxide in methanol at room temperature under nitrogen for 15 minutes. Saturated aqueous sodium chloride (5 ml) was then added, the mixture was extracted with ether (3×10 ml). The combined extract was washed with water (2×5 ml), saturated aqueous sodium chloride (2×5 ml), then dried over anhydrous magnesium sulfate, filtered, and concentrated in vacuo. The isomers cis and trans were separated by high performance liquid chromatography (HPLC; Zorbax Sil semipreparative column, 6.2 mm×25 cm) using 5% isopropanol-hexane to give compound 3b ($R_1$=isobutyl, $X_1$, $X_2$, $X_3$=H, 23R-stereochemistry): UV ($C_2H_5OH$) $\lambda_{max}$ 265 nm; mass spectrum, m/e (relative intensity) 416 (M+, 17), 398 (12), 380 (5), 152 (38), 134 (100); NMR (CDCl$_3$) $\delta$0.58 (s, 18—H$_3$), 0.92 (d, J=6.4 Hz, 26—H$_3$ and 27—H$_3$), 0.98 (d, J=6.4 Hz, 21—H$_3$), 3.79 (m, 23—H), 4.24 (m, 3—H), 4.44 (m, 1—H), 5.01 (br s, 19Z—H), 5.33 (br s, 19E—H), 6.03 (d, J=11.2 Hz, 7—H), 6.39 (d, J=11.2 Hz, 6—H), and the 5,6-trans compound 4b ($R_1$=isobutyl, $X_1$, $X_2$, $X_3$=H, 23R-stereochemistry): UV ($C_2H_5OH$) $\lambda_{max}$ 273 nm; mass spectrum, m/e (relative intensity) 416 (M+, 9), 398 (5), 152 (29), 134 (100); NMR (CDCl$_3$) $\delta$0.61 (s, 18—H$_3$), 0.93 (d, J=6.8 Hz, 26—H$_3$ and 27—H$_3$O, 0.99 (d, J=6.8 Hz, 21—H$_3$), 3.79 (m, 23—H), 4.24 (m, 3—H), 4.50 (m, 1—H), 4.98 (d, J=1.2 Hz, 19Z—H), 5.13 (d, J=1.2 Hz, 19E—H), 5.89 (d, J=11.2 Hz, 7—H), 6.59 (d, J=11.2 Hz, 6—H), as well as the 23S-isomer of 3b: UV ($C_2H_5OH$) $\lambda_{max}$ 265 nm; mass spectrum, m/e (relative intensity) 416 (M+, 24) 398 (89), 380 (35), 152 (100), 134 (73).

EXAMPLE 7

Preparation of compound 3d ($R_1$=$R_2$=Me) from 23-ester

Methylmagnesium bromide (CH$_3$MgBr; 0.05 ml, 3 mole solution in ether) was added dropwise to a solution of (5Z,7E)-(1S,3R)-1,3-dihydroxy-24-nor-9,10-seco-5,7,10(19)-cholatrien-23-oic acid methyl ester (1 mg) in ether (5 ml) under nitrogen. The mixture was heated at reflux for 10 minutes, cooled, and saturated aqueous ammonium chloride was added slowly. The reaction mixture was worked up in the usual way, and the product was purified by high performance liquid chromatography (HPLC; Microporasil semipreparative column) using 8% isopropanol to afford compound 3d ($R_1$=$R_2$=Me, $X_1$=$X_2$=$X_3$=H) (Rd 0.48 on silica gel in 15:85 methanol-chloroform): UV ($C_2H_5OH$) $\lambda_{max}$ 265 nm; mass spectrum, m/e (relative intensity) 388 (M+, 7), 370 (52), 352 (50), 337 (9), 269 (11), 267 (9), 251 (15), 152 (31), 134 (100); NMR (CDCl$_3$) $\delta$0.60 (s, 18—H$_3$), 1.08 (d, J=6.4 Hz, 21—H$_3$), 1.24 (s, 26—H$_3$ and 27—H$_3$), 4.25 (m, 3—H), 4.45 (m, 1—H), 5.02 (br s, 19Z—H), 5.35 (br s, 19E-h), 6.04 (d, J=12.0 Hz, 7—H), 6.40 (d, J=12.0 Hz, 6—H).

EXAMPLE 8

Preparation of compound 3b ($R_1$=H) from 23-ester

Lithium aluminum hydride, saturated in ether, was added slowly to a stirred solution of (5Z,7E)-(1S,3R)-1,3-dihydroxy-24-nor-9,10-seco-5,7,10(19)-cholatrien-23-oic acid methyl ester (1 mg) in ether (2 ml) at room temperature under nitrogen. The reaction was allowed to proceed for 5 minutes. The usual workup, followed by high performance liquid chromatography (HPLC; Microporasil semipreparative column) using 8% isopropanol-hexane, produced compound 3b ($R_1$=H; $X_1$=$X_2$=$X_3$=H) (Rf 0.45 on silica gel in 15:85 methanol-chloroform): UV ($C_2H_5OH$) $\lambda_{max}$ 265 nm; mass spectrum, m/e (relative intensity) 360 (M+, 8), 342 (51), 324 (49), 269 (11), 251 (25), 152 (33), 134 (100); NMR (CDCl$_3$) $\delta$0.58 (s, 18—H$_3$), 0.98 (d, J=6.2 Hz, 21—H$_3$), 3.71 (br m, 23—H$_2$), 4.25 (m, 3—H), 4.45 (m, 1—H), 5.03 (br s, 19Z—H), 5.34 (br s, 19E—H), 6.03 (d, J=11.2 Hz, 7—H), 6.40 (d, J=11.2 Hz, 6—H).

EXAMPLE 9

Oxidation of 1b to 1c

A stirred solution of the cyclovitamin D-23-alcohol (3b, $R_1$=isobutyl, Z=methyl) (1 equivalent) in dry N,N-dimethylformamide (1 ml) was cooled on an ice bath under nitrogen before pyridinium dichromate (7 equivalent) was added. The reaction was allowed to proceed at 5° C. under nitrogen for 8 hr., then the mixture was poured over ice water (3 ml) and extracted with ether (3×5 ml). The combined extract was washed sequentially with water (1×3 ml) and saturated aqueous sodium chloride, then dried over anhydrous magnesium sulfate, filtered, and concentrated in vacuo. Chromatography on silica gel using 30% ethyl acetate-hexane provided the ketone 3c ($R_1$=isobutyl, Z=methyl); mass spectrum, m/e (relative intensity) 412 (M+, 25), 380 (32), 365 (7), 161 (36), 150 (66), 135 (20), 133 (19), 131 (21), 121 (27), 119 (46), 118 (100).

EXAMPLE 10

Alkylation of 1c to 1d

Methylmagnesium bromide (CH$_3$MgBr, 2.8M solution in ether; 20 equivalent) was added to a stirred solution of the ketone 1c ($R_1$=isobutyl, Z=methyl) in ether (0.5 ml) at room temperature under nitrogen. The mixture was heated at reflux overnight, cooled, and treated with saturated aqueous ammonium chloride until a clear precipitate separated. The supernatant was then decanted, the precipitate was washed with fresh ether, and the combined ethereal solutions were dried over anhydrous magnesium sulfate, filtered, and concentrated in vacuo. Chromatography on silica gel using 30% ethyl acetate-hexane provided the tertiary alcohol 1d ($R_1$=isobutyl, $R_2$=methyl, $X_3$=H, Z=methyl); mass spectrum, m/e (relative intensity) 428 (M+, 21), 410 (8), 396 (7), 381 (7), 150 (46), 135 (20), 133 (26), 131 (27), 121 (26), 119 (49), 118 (75).

EXAMPLE 11

Conversion of 1d to 3d and 4d

Treatment of compound 1d ($R_1$=isobutyl, $R_2$=methyl, Z=methyl) as obtained in Example 10, with selenium dioxide and tert-butyl hydroperoxide, under the conditions described in Example 5, provides the corresponding 1α-hydroxy-derivative 2d ($R_1$=isobutyl, $R_2$=methyl, $X_1$=H, and Z=methyl). Solvolysis of this material, followed by acyl hydrolysis and separation of cis and trans isomers, as described in Example 6, gives compound 3d ($R_1$=isobutyl, $R_2$=methyl, $X_1$=$X_2$=$X_3$=H) and compound 4d ($R_1$=isobutyl, $R_2$=methyl, $X_1$=$X_2$=$X_3$=H).

EXAMPLE 12

Conversion of 1c to 3c and 4c

Compound 1c ($R_1$=isobutyl, Z=methyl) as obtained in Example 9 is converted to the 1α-hydroxy derivative 2c ($R_1$=isobutyl, $X_1$=H, Z=methyl) under conditions analogous to those described in Example 2. Compound 2c is solvolyzed using the conditions described in Example 3 to obtain in admixture the acetates 3c and 4c (where $R_1$=isobutyl, $X_1$=H, $X_2$=acetyl). The acetates are hydrolyzed as described in Example 3 and the corresponding free hydroxy compounds are separated by high performance liquid chromatography to obtain compound 3c ($R_1$=isobutyl, $X_1$=$X_2$=H), and 4c ($R_1$=isobutyl, $X_1$=$X_2$=H).

EXAMPLE 13

Reduction of 3a and 4a to 3b and 4b

Aldehyde 3a ($X_1$=$X_2$=H) in diethyl ether was treated with an alcoholic solution of $NaBH_4$. After 1 hr. the reaction mixture was worked up in the usual fashion, to obtain after thin layer chromatographic purification of the product, the 23-alcohol 3b ($R_1$=H, $X_1$=$X_2$=$X_3$=H) identical with the material obtained in Example 8. The exactly analogous reduction of the 5,6-trans-23-aldehyde 4a ($X_1$=$X_2$=H) provides the 5,6-trans-alcohol of structure 4b ($R_1$=H, $X_1$=$X_2$=$X_3$=H).

EXAMPLE 14

Alkylation of compound 3a to 3b

A stirred solution of the aldehyde 3a ($X_1$=$X_2$=H) (1 equivalent) in ether (0.5 ml) was treated with ethylmagnesium bromide ($C_2H_5MgBr$, 2.8M solution in ether; 20 equivalent) at room temperature under nitrogen for 4 hr. Saturated aqueous ammonium chloride was added dropwise. The usual workup then gave the 23-alcohol (3b, $R_1$=ethyl, $X_1$=$X_2$=$X_3$=H); mass spectrum, m/e (relative intensity) 388 (M+, 11), 370 (6), 357 (3), 152 (34), 134 (100).

We claim:

1. Compounds selected from the group consisting of

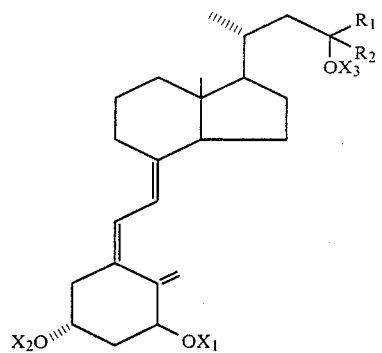

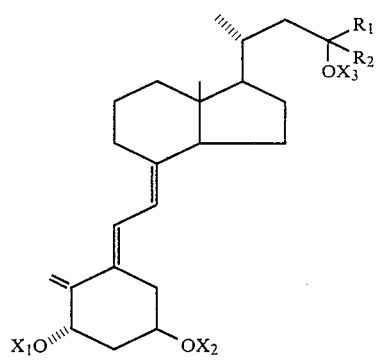

wherein $R_1$ and $R_2$ are each selected from the group consisting of hydrogen and alkyl, and where $X_1$, $X_2$, and $X_3$ are selected from the group consisting of hydrogen and acyl.

2. Compounds according to claim 1 wherein $R_1$ and $R_2$ are both hydrogen.

3. A compound according to claim 2 wherein each of $X_1$, $X_2$ and $X_3$ is hydrogen.

4. Compounds according to claim 1 wherein each of $R_1$ and $R_2$ is alkyl.

5. A compound according to claim 4 wherein $R_1$ and $R_2$ are methyl and $X_1$, $X_2$, $X_3$ are hydrogen.

6. Compounds according to claim 1 wherein $R_1$ is alkyl and $R_2$ is hydrogen.

7. Compounds according to claim 6 wherein $R_1$ is selected from methyl, ethyl, or propyl.

8. Compounds according to claim 6 wherein $R_1$ is isobutyl.

9. 1,23-dihydroxyvitamin $D_3$.

10. 1,23-dihydroxy-5,6-trans vitamin $D_3$.

11. Compounds selected from the group consisting of

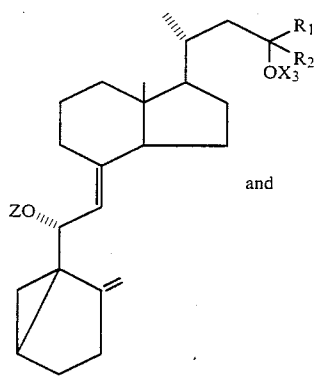

and

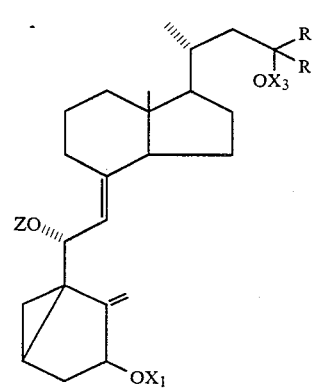

wherein Z is alkyl and each of $X_1$ and $X_3$ are hydrogen or acyl and where each of $R_1$ and $R_2$ is selected from the group consisting of hydrogen and alkyl.

12. Compounds according to claim 11 wherein Z is methyl.

13. Compounds according to claim 12 where $R_1$ and $R_2$ are both hydrogen.

14. Compounds according to claim 12 wherein $R_1$ is alkyl and $R_2$ is hydrogen.

15. Compounds according to claim 12 where $R_1$ and $R_2$ are alkyl.

16. Compounds selected from the group consisting of

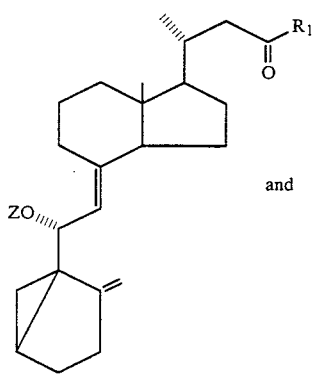

and

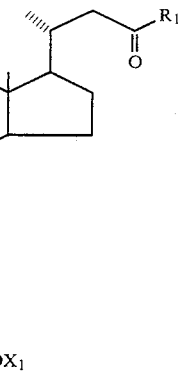

wherein Z is alkyl, $X_1$ is hydrogen or acyl and $R_1$ is hydrogen or alkyl.

17. Compounds according to claim 16 where Z is methyl.

18. Compounds according to claim 17 where $R_1$ is hydrogen.

19. Compounds according to claim 17 where $R_1$ is alkyl.

20. Compounds according to claim 19 where $R_1$ is isobutyl.

21. Compounds selected from the group consisting of

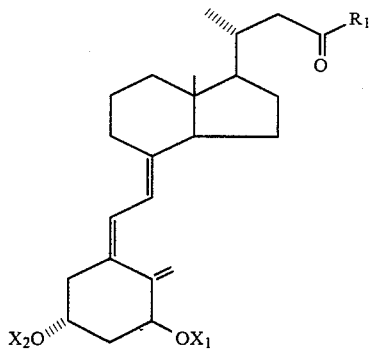

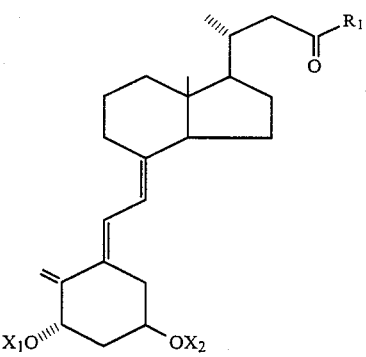

wherein $X_1$ and $X_2$ are hydrogen or acyl and $R_1$ is hydrogen or alkyl.

22. Compounds according to claim 21 where $R_1$ is hydrogen.

23. Compounds according to claim 21 where $R_1$ is alkyl.

24. A compound according to claim 22 where $X_1$ and $X_2$ are hydrogen.

25. A compound according to claim 23 where $X_1$ and $X_2$ are hydrogen.

26. A process for preparing the compounds of claim 1 which comprises subjecting a cyclovitamin D compound having the formula

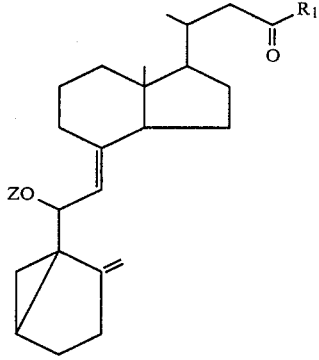

wherein $R_1$ is selected from hydrogen or alkyl and Z is alkyl to reduction with a hydride reducing reagent or to a reaction with an alkyl Grignard reagent, thereby obtaining a compound having the formula

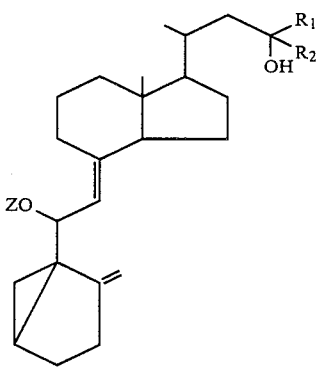

wherein each of $R_1$ and $R_2$ is hydrogen or alkyl and Z is alkyl, subjecting said compound, or, optionally, said 23-acyloxy derivative obtained by acylating said compound, to $1\alpha$-hydroxylation treatment with $SeO_2$ and a hydroperoxide to obtain the corresponding $1\alpha$-hydroxylated compound, subjecting said $1\alpha$-hydroxy derivative to solvolysis in a medium containing an organic acid whereby the 5,6-cis and 5,6-trans compounds having the formula

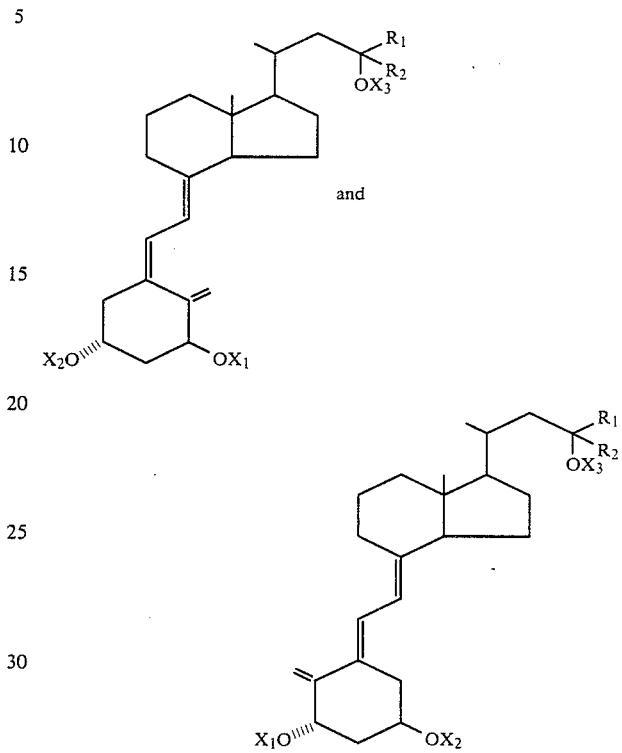

wherein $R_1$ and $R_2$ have the meaning defined above, $X_1$ is hydrogen, $X_2$ is acyl and $X_3$ is hydrogen or acyl are obtained in admixture, separating said compounds and, optionally, either removing any acyl groups present to obtain the corresponding free hydroxy compound, or, acylating free-hydroxy groups to obtain the corresponding acyloxy derivative.

27. The process of claim 25 wherein acyl removal of any acyl groups precedes separation of the 5,6-cis and 5,6-trans compounds.

28. The process of claims 25 wherein the $1\alpha$-hydroxylation solvolysis is carried out prior to the reduction or Grignard-reaction step.

* * * * *

UNITED STATES PATENT OFFICE
CERTIFICATE OF CORRECTION

Patent No. 4,512,925      Dated April 23, 1985

Inventor(s) Hector F. DeLuca et al

It is certified that error appears in the above-identified patent and that said Letters Patent are hereby corrected as shown below:

Insert the following paragraph as the first paragraph of the specification in Column 1:

--This invention was made with Government support under NIH Grant No. AM-14881 awarded by the Department of Health and Human Services. The Government has certain rights in this invention.--

*Signed and Sealed this*

*Twenty-fourth* Day of *September 1985*

[SEAL]

*Attest:*

DONALD J. QUIGG

*Attesting Officer*     *Commissioner of Patents and Trademarks—Designate*